United States Patent [19]

Hannun et al.

[11] Patent Number: 5,369,030
[45] Date of Patent: Nov. 29, 1994

[54] METHOD OF INDUCING CELLULAR DIFFERENTIATIONS AND ALTERING CELL PHENOTYPE USING CERAMIDE ANALOGS

[75] Inventors: Yusuf A. Hannun, Chapel Hill; Alicja Bielawska, Apex, both of N.C.

[73] Assignee: Duke University, Durham, N.C.

[21] Appl. No.: 944,100

[22] Filed: Sep. 11, 1992

[51] Int. Cl.$^5$ .................. C12N 5/00; A61K 31/16
[52] U.S. Cl. ................. 435/240.2; 435/240.1; 514/625; 514/629; 544/168
[58] Field of Search ............... 514/625, 629; 544/168; 435/240.2, 240.1

[56] References Cited

U.S. PATENT DOCUMENTS 4,816,450  3/1989  Bell ............................ 514/25

OTHER PUBLICATIONS

Abstract, Warren et al., 1976.
Bielawska et al., *Ceramide-mediated . . . , 1992, 18493–18497.*
Okzaki et al., *Role of Ceramide . . . , 1990, pp. 15823–15831.*
Merrill et al., *Inhibition of Phorbol . . . , 1986, 12610–12615.*
Jung Hyun et al., *Synthetic Inhibitors . . . , 1975* vol. 166, pp. 382–389.
Wainer et al., *Application of High . . . 259 (1983) 465–472.*
Goodwin, B. J. et al. (1982) *J. Clin. Invest.* 70:699–706.
Arora, R. C. et al. (1972) *Journal of Lipid Research* 13:86–91.
Shapiro, D. et al. (1961) *J. Am. Chem. Soc.* 83:3327–3332.
Pick, Edgar et al. (1981) *Immunol. Methods* 46:211–226.
Hannun, Y. A. and Bell, R. M. (1989) *Science* 243:500–507.
Hannun, Y. A. et al. (1986) *J. Biol Chem.* 261:12604–12609.
Hannun, Y. A. and Bell, R. M. (1987) *Science* 235:670–674.
Hannun, Y. A. et al. (1987) *J. Biol. Chem.* 262:13620–13626.
Wilson, E. et al. (1987) *Arch. Biochem. Biophys.* 259:204–214.
Okazaki et al. (1990) *J. Biol. Chem.* 285:15823–15831.
Collins, S. J. (1987) *Blood* 70:1233–1244.
Okazaki et al (1989) *J. Biol. Chem.* 254:19076–19080.

*Primary Examiner*—David M. Naff
*Assistant Examiner*—Deborah K. Ware
*Attorney, Agent, or Firm*—Woodcock, Washburn, Kurtz Mackiewicz & Norris

[57] ABSTRACT

The present invention provides methods and pharmaceutical preparations of N-acyl-phenylaminoalcohol analogs for inducing differentiation of cells. Compositions having the formula

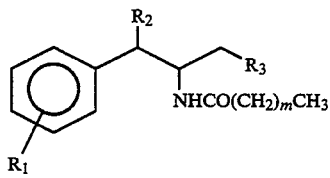

wherein
$R_1$ is H, $NO_2$, OH, chlorine, bromine or fluorine;
$R_2$ is H, OH or methoxy;
$R_3$ is H or OH; and
m is from about 10 to about 14 are administered to cells of a mammal that are capable of undergoing differentiation in amounts effective to induce differentiation of the cells. The invention also provides methods and pharmaceutical preparations for altering the phenotype of cells and for treating diseases characterized by hyperproliferation of cells.

17 Claims, No Drawings

METHOD OF INDUCING CELLULAR DIFFERENTIATIONS AND ALTERING CELL PHENOTYPE USING CERAMIDE ANALOGS

REFERENCE TO GOVERNMENT SUPPORT

The research disclosed in the present patent application was supported in part by National Institutes of Health grant GM43825. The United States government has certain rights in the invention.

FIELD OF THE INVENTION

The present invention relates to the field of compounds capable of inhibiting cell growth and/or differentiation. More particularly the present invention is concerned with the use of N-acyl-phenylaminoalcohols to inhibit cell growth and/or induce cell differentiation.

BACKGROUND OF THE INVENTION

A number of human malignant and non-malignant diseases have as one of their distinguishing features the hyperproliferation of cells. In these diseases, cells proliferate at abnormally high rates. The cells found in cancerous tumors and leukemias grow and divide uncontrollably, which accounts in part for their rapid spread in the body. Similarly, with some non-malignant diseases such as psoriasis, the cells also grow and divide at abnormally high rates. In these diseases, the hyperproliferating cells are present in a relatively undifferentiated state. Undifferentiated cells are able to grow and divide. Once a cell differentiates, however, it loses the ability to proliferate. Some proposed treatments have been aimed towards inducing cell differentiation to stop cell proliferation, and thus bring the diseases under control.

Recently it has been found that sphingolipids play important roles in cell growth, oncogenesis, and differentiation (Hannun, Y. A. and Bell, R. M. (1989) Science 243: 500–507). At least 300 different sphingolipids are synthesized in various mammalian cell types. Structurally, sphingolipids are composed of a long-chain sphingoid base, an amide-linked fatty acid, and a polar head group at the 1-position. Except for ceramide, which has hydroxyl at the 1-position, and for sphingolmyelin, which has a phosphorylcholine head group, all other sphingolipids contain carbohydrate head groups and hence are designated glycosphingolipids. Sphingolipid breakdown products are emerging as a novel class of cell regulatory molecules. Sphingolipid breakdown products, sphingosine and ysosphingolipids, inhibit protein kinase C, believed to be a pivotal enzyme in cell regulation and signal transduction (Hannun, Y. A. et al. (1986) *J. Biol Chem.* 261: 12604–12609). Sphingolipids and lyso-sphingolipids affect significant cellular responses and exhibit anti-tumor promoter activities in various mammalian cells (Hannun, Y. A. and Bell, R. M. (1987) Science 235: 670–674; Hannun, Y. A. et al. (1987) *J. Biol. Chem.* 262: 13620–13626; and Wilson, E. St al. (1987) Arch. Biochem. Biophys. 259: 204–214).

U.S. Pat. No. 4,816,450 issued Mar. 28, 1989 to Bell discloses long chain bases, generally sphingosine and sphingosine derivatives, useful for inhibiting protein kinase C. Activation of protein kinase C has been identified as fundamental to tumor promotion, cellular transformation and to understanding the inhibition by anti-tumor agents.

It has also been found that ceramide and cell-permeable ceramides with shorter N-acyl chains are potent regulators of cell differentiation as disclosed in co-pending application Ser. No. 566,978 filed Aug. 13, 1990 and in Okazaki et al. (1990) J. Biol. Chem. 285: 15823–1583. Exposure of cells to exogenously applied ceramide and such derivatives induces cell differentiation.

Interferon which induces cell differentiation has been tested for treatment of tumors. Similarly, vitamin $D_3$ which induces differentiation of HL-60 cells, a human myelocytic leukemia cell line, has also been tested for tumor treatment.

Despite efforts in developing treatments for diseases characterized by cellular hyperproliferation, there is still a need for treatments for these diseases.

Accordingly, it is an object of the invention to provide methods and compositions for inducing cell differentiation and/or inhibition of cell growth. It is a further object to provide methods and pharmaceutical compositions for treating diseases characterized by hyperproliferation of cells. Other objects of the present invention will become apparent from a review of the specification and appended claims.

SUMMARY OF THE INVENTION

The present invention provides compounds for inducing cell differentiation and/or inhibiting cell growth having the formula:

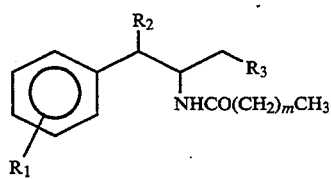

wherein
$R_1$ is H, $NO_2$, OH, chlorine, bromine or fluorine;
$R_2$ is H, OH or methoxy;
$R_3$ is H or OH; and
m is an integer ranging from about 10 to about 214 (hereinafter Formula I). Accordingly, the present invention also provides methods for inducing cell differentiation comprising adding to a mammalian cell capable of undergoing differentiation a compound of Formula I as defined herein in an amount effective to induce differentiation of the cell.

In other aspects of the present invention, methods of altering the phenotype of a cell are provided comprising adding to a mammalian cell having a transformed phenotype a compound having Formula I in an amount effective to alter the phenotype of the cell to a non-transformed phenotype.

Methods of treating diseases characterized by hyperproliferation of cells are also provided in further aspects of the present invention wherein a therapeutically effective amount of a compound having Formula I is administered to a mammal suspected of having such disease.

An additional aspect of the invention provides a method of slowing cell growth comprising adding or administering to cells an amount of a compound of Formula I effective to slow cell growth. Compounds having Formula I may also be added to cells in a mammal in an amount effective to slow cell growth.

In another aspect of the present invention methods of palliating the effects of aging on the skin are provided wherein compounds having Formula I may be administered to the skin in an amount effective to reduce the effects of aging.

Pharmaceutical compositions comprising compounds having Formula I in a pharmaceutically acceptable carrier are also provided in yet additional aspects of the present invention.

This invention is more particularly pointed out in the appended claims and is described in its preferred embodiments in the following description.

DETAILED DESCRIPTION OF THE INVENTION

Applicants have discovered that administration of certain N-acyl-phenylaminoalcohol analogs of ceramide induces differentiation of HL-60 cells, a line of myelocytic leukemia cells. Administration of N-acyl-phenylaminoalcohol ceramide analogs slows proliferation of the cells and induces the cells to display a differentiated phenotype indicative of normal monocyte cells. It is believed that this effect will be manifested in other types of cells as well.

The human cell line HL-60, originally isolated from a patient with acute myelocytic leukemia, is frequently used to study myeloid cell differentiation. These cells can be induced to mature into granulocytes when treated with agents such as dimethyl sulfoxide or retinoic acid or into monocyte/macrophage-like cells upon incubation with phorbol esters, 1α,25-dihydroxyvitamin D3, or ganglioside $G_{M3}$. The mechanism by which maturation is caused by most of these compounds is not known. For a review of the characteristics of the HL-60 promyelocytic leukemia cell line and its use as a model for the study cell of differentiation see Collins, S. J. (1987) Blood 70: 1233-1244. This well-known cell model has been used to show the usefulness of the compounds of this invention for treating diseases characterized by cell hyperproliferation.

N-acyl-phenylaminoalcohol analogs of ceramide encompassed by methods and preparations of the present invention have the formula:

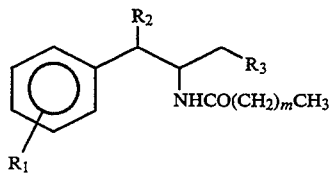

wherein
$R_1$ is H, $NO_2$, OH, chlorine, bromine or fluorine;
$R_2$ is H, OH or methoxy;
$R_3$ is H or OH; and
m is an integer ranging from about 10 to about 14 (hereinafter Formula I).

$R_1$ is preferably H, $NO_2$, OH, chlorine, bromine or fluorine. More preferably $R_1$ is H or $NO_2$. $R_1$ can be situated at any position on the phenyl ring of Formula I, preferably at the 4' position. $R_2$ is preferably H, OH or methoxy. $R_3$ is preferably H or OH.

Applicants have found that neither the primary ($R_3$) nor secondary ($R_2$) alcohol is necessary to inhibit HL-60 cell growth and induce cell differentiation.

The amide-linked acyl chain has been found to be necessary to activity. Chain length of the acyl chain may be represented by Cn where n may range from about 12 to about 16. Referring to Formula I, m (which is n−2) is preferably from about 10 to about 14. In preferred embodiments of the invention, m is 10 or 12. Most preferably m is 12.

Table I sets forth some preferred N-acyl phenylaminoalcohols of Formula I useful in the methods and pharmaceutical preparations of the invention.

The important role of the of the chiral center of carbon 1 of Formula I has been identified by Applicants for APP-1 stereoisomers. C14-D-erythro-APP-1 was the most active of the APP-1 stereoisomers, exhibiting approximately 15% of control cell growth. Its enantiomer, C14-L-erythro-APP-1 showed little activity (87% of control cell growth). The racemic mixture of C14-DL-erythro-APP-1 showed intermediate activity of 60% of control cell growth. The D-threo isomer, C14-D-threo-APP-1 had intermediate activity of 49% of control cell growth.

Thus, for any particular compound useful in the methods and pharmaceutical compositions of the invention, one or more isomers of the compound may have greater activity than other isomers. Accordingly, any isomer of APP-1 alone or in combination with one or more other isomers of APP-1 can be used in the pharmaceutical compositions and methods of the present invention. Additionally, the methods of the present invention can be practiced with one, or a combination of two or more of the compounds of Formula I or isomeric forms thereof, and the pharmaceutical compositions of the invention can be formulated with one or a combination of two or more of

TABLE I

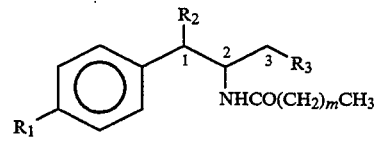

| Abbreviation | $R_1$ | $R_2$ | $R_3$ | Configuration (R, S) | Phenylaminoalcohol Base |
|---|---|---|---|---|---|
| C14-L-t-APPD | H | OH | OH | 1S, 2S | L-threo-2-amino-1-phenyl-1,3-propandiol |
| C14-D-t-ANPPD | $NO_2$ | OH | OH | 1R, 2R | D-threo-2-amino-1-(4'-nitrophenyl)-1,3-propandiol |
| C14-D-e-APP-1 | H | OH | H | 1S, 2R | D-erythro-2-amino-1-phenyl-1-propanol |
| C14-L-e-APP-1 | H | OH | H | 1R, 2S | L-erythro-2-amino-1-phenyl-1-propanol |
| C14-D-t-APP-1 | H | OH | H | 1R, 2R | D-threo-2-amino-1-phenyl-1-propanol |
| C14-DL-e-APP-1 | H | OH | H | (1R, 2S), (1S, 2R) | DL-erythro-2-amino-1-phenyl-1-propanol |
| C14-L—APP-3 | H | H | OH | 2S | L-2-amino-3-phenyl-1-propanol |
| C14-D—APP-3 | H | H | OH | 2R | D-2-amino-3-phenyl-1-propanol | the compounds of Formula I or isomeric forms thereof.

The term "APP" is used herein to refer to 2-amino-1-phenyl-1-propanol. "APP-1" refers to 2-amino-1-phenyl-1-propanol. "APP-3" refers to 2-amino-3-phenyl-1-propanol. The term "APPD" refers to 2-amino-1-phenyl-1,3-propanediol. "ANPPD" is used to refer to 2-amino-1--(4'-nitrophenyl)-1,3-propanediol. D and L refer to the relative configuration of the enantiomer. Similarly, "3" and "t" refer to threo- or erythro- diastereomers respectively. Cn refers to the number of carbons in the N-acyl group, where n is m+2. For example, C14 as used in Table I refers to an N-acyl group comprising a total of 14 carbons. In this instance, m is 12. The carbons of the phenylaminoproanediol backbone are labeled 1, 2, and 3. The 1 and 2 carbons are chiral. For example, the abbreviation C14-L-e-APP-1 refers to the L-erythro isomer (L-e) of 2-amino-1-phenyl-1-propanol (APP-1) having an N-acyl chain 14 carbons in length (C14, m=12).

In accordance with methods of the present invention, compounds having Formula I are added to cells capable of differentiation, or administered to cells capable of differentiation in a mammal, usually a human patient, in an amount effective to induce differentiation of the cells. The terms cellular differentiation, differentiation of cells and similar terms are intended to refer to the biological process wherein cells mature and acquire the characteristics of a mature cell. During differentiation the cell may, for example, acquire or lose morphological shape or characteristics, and gain or lose the ability to bind substances or perform chemical reactions. The term inducing differentiation is intended to refer to the acts of manipulating cells that are capable of differentiation to acquire a differentiated phenotype. Generally, mammalian cells begin as immature, undifferentiated cells that then undergo differentiation during which time they acquire the characteristics of mature, differentiated cells.

In accordance with other embodiments of the invention, the phenotype of a cell is altered by adding a compound having Formula I to cells having a transformed phenotype, or administering to transformed cells in a mammal, usually a human patient, in an amount effective to alter the phenotype of the cell to a phenotype associated with normal cells of the same kind. The shape, behavior and other characteristics of a cell including biochemical activities are generally known as the phenotype of a cell. The "normal" phenotype of a cell refers to a cell that appears normal by conventional criteria such as shape, markers of cell type, growth, response to environment, and regulation of cellular metabolic pathways. Transformed cells are cells that have been derived from normal cells, either spontaneously or by manipulation, that have acquired cancer-like properties such as more immature/undifferentiated phenotype, increased growth, poor or no response to environment and to controls of cell growth, or the ability to cause tumors in animal models. Altering the phenotype of a cell thus refers to the acts of changing at least one characteristic of the cell, including the ability to bind compounds, express enzymatic activity, respond to its environment and other cellular characteristics.

Because of the ability of the compounds of this invention to to induce cell differentiation and/or alter the phenotype of cells, such compounds are expected to be useful for treatment of diseases characterized by hyperproliferation of cells, or where there is significant disturbance in differentiation of cells. Diseases characterized by hyperproliferation of cells include diseases wherein one of the consequences or manifestations of the disease is abnormal proliferation of the involved cells. Thus, another aspect of the present invention provides methods of treating diseases characterized by hyperproliferation of cells wherein compounds having Formula I are administered to a mammal suspected of having such disease in a therapeutically effective amount.

Abnormal proliferation of cells is generally manifested by an increase in the number of cells present when compared to the number of cells present in the absence of disease. Hyperproliferation of cells may occur in normal, abnormal or malignant cells. Diseases characterized by hyperproliferation of cells include cancerous tumors, leukemias, non-malignant tumors, psoriasis, atherosclerosis and other diseases. This list is intended to be illustrative only and is not intended to be exclusive. These diseases share in the fact that they are primarily caused by increased and abnormal proliferation of either malignant (e.g. cancer, leukemia and lymphoma), premalignant (e.g. myelodysplasia), or benign (e.g. lymphoproliferative, benign tumors, and psoriasis) cells. Inhibition of cell proliferation by methods of the present invention may slow the growth of affected cells in these diseases yielding a significant therapeutic and potentially curative effect.

Many disorders of this type are also characterized by having undifferentiated cells. Undifferentiated cells or undifferentiated phenotype refers to immature cells that are usually unable to function as mature cells because they lack the necessary biochemical and physiological machinery characteristic of mature cells. During the process of cell differentiation, immature cells begin to express the biochemical and physiological characteristics of mature cells. For example, in vivo, stem cells differentiated into granulocytes, and monocytes. The inability of undifferentiated cells to change into more differentiated cells having a mature phenotype contributes to the lack of normal function.

Methods of the invention, directed to inducing differentiation should also help in attenuating the increased proliferation of these cells and in allowing the cells to acquire the necessary biochemical and phenotypic characteristics that allow them to function as normal cells. For example, in the case of psoriasis, by methods of this invention, differentiation of the abnormal proliferating cells in psoriasis may be induced which should allow the cells to differentiate into healthy skin. Similarly, in myelodysplasias, these methods may cause differentiation of early and undifferentiated myeloid cells which may play a significant role in combating the main health hazards from these disorders, i.e. the decreased numbers of normal, well-differentiated blood cells.

Leukemia, lymphoma, and other forms of cancer may also be treated by increasing the differentiation of those malignant cells. Since differentiated cells are usually unable to divide, this helps in treating those diseases since the individual cells will no longer be able to replenish the malignant clone and will not be able to metastasize.

Furthermore, application of methods of the present invention to a wide array of neoplastic disease is also strongly supported by the observations that both tumor necrosis factor (TNF) and gamma interferon elevate the levels of ceramide and that ceramide may mediate the effects of these agents on HL60 cell differentiation. Therefore, addition of compounds having Formula I to cells may similarly mediate the effects of tumor necrosis factor and gamma interferon.

It is also believed that methods of the present invention may be useful in inducing immunosuppression in mammals, particularly humans by slowing the growth of lymphocytes. Other agents that suppress the growth of lymphocytes such as steroids, anti-lymphocyte antibodies, and others play important roles in inducing immunosuppression. Immunosuppression is very important in organ rejection such as occurs in renal transplant, heart transplant, liver transplant and other organ transplant. Also, since steroids increase ceramide, ceramide may mimic the effects of steroids as immunosuppressants. The slowing of the growth of cells, particularly lymphocytes, refers to retarding or inhibiting the normal rate of growth and cell division of the cells. Thus methods effective to slow the growth of cells have the effect of slowing the rate of growth and normal function of those cells.

Auto-immune disorders are characterized by increased activity and proliferation of self-reactive lymphocytes. The ability of ceramide to potentially suppress growth of lymphocytes is expected to significantly contribute to suppressing manifestations of auto-immune disorders. Since corticosteroids increase the levels of ceramide, and corticosteroids have a therapeutic role in autoimmune disorders, it is now believed that in accordance with methods of the present invention the addition of the ceramide analogs, N-acyl phenylaminoalcohols, to cells may mediate the action of steroids in these disorders.

Obesity may also be characterized by increased proliferation and metabolism of fat cells in the body. By methods of the present invention the growth of these cells may be slowed, thus contributing to the reduction of obesity. A major connection arises from the fact that tumor necrosis factor increases the levels of ceramide. TNF is postulated to play a role in inducing cachexia and has been implicated as a potential therapy for obesity. It is now believed that in accordance with methods of the present invention ceramide analogs, N-acyl phenylaminoalcohols may be administered for treatment of obesity.

Atherosclerosis is another disease characterized by increased and possibly abnormal proliferation of smooth muscle cells and endothelial cells. It is expected that slowing the growth of these cells by methods of this invention will contribute to the control of atherosclerosis.

Methods of the present invention are also expected to be useful to prevent skin aging. Retinoic acid, which is known for use in anti-skin aging treatments, elevates the levels of ceramide in skin cells. Ceramide analogs, N-acyl phenylamino alcohols may be administered in accordance with methods of the present invention to mediate the action of retinoic acid and be useful in anti-aging skin treatments.

The present invention may also be useful in chemoprevention, i.e. the treatment of cells to prevent or slow the change of the cells from a normal phenotype to a transformed malignant phenotype. The compounds of the present invention are able to induce differentiation of malignant cells and otherwise undifferentiated cells, thus methods of the present invention are believed to be useful in inducing and slowing the proliferation of early (clinically undetectable) malignant cells. This would constitute a strong chemopreventive therapy. Similarly, retinoic acid may be useful as a chemopreventive agent, thus since retinoic acid elevate levels of ceramide, methods of the invention may also be useful for chemoprevention along this route.

Compounds of the invention can be prepared from readily available materials according to the method disclosed herein wherein a phenylaminoalcohol is reacted with an acyl chloride having a desired chain length to yield the compounds of the invention. Other methods known in the art may also be used to prepare the compounds of the invention.

A further aspect of the invention provides pharmaceutical preparations comprising a compound having Formula I and a pharmaceutically acceptable carrier or diluent. The pharmaceutical compositions of the invention may be used to treat mammals such as man, which are afflicted with the various conditions described herein and others which are caused by defective differentiation processes, and are also useful the other aspects of the present invention.

In accordance with methods of the present invention compounds having Formula I may be administered to a mammal having a disease, or suspected of having a disease, singly or in combination with other compounds having Formula I or other therapeutic or palliative agents. Compounds having Formula I may be administered in any mode, such as orally, parenterally, intradermally, intramuscularly, intravenously, subcutaneously or topically. The actual route can readily be determined by analogy to known methodologies and will depend on such factors as the particular disease state being treated, its severity, and the age and condition of the patient.

For injection purposes, the medium used is preferably a sterile liquid. As an injection medium, it is preferred to use water which contains the stabilizing agents, solubilizing agents and/or buffers conventional in the case of injection solutions. Desirable additives include, for example, tartrate and borate buffers, ethanol, dimethylsulfoxide, complex forming agents (for example, ethylenediaminetetraacetic acid) high molecular weight polymers (for example polyethylene oxide) for viscosity regulation or polyethylene derivatives of sorbitan anhydrides.

The total routine (e.g., daily, weekly, monthly, etc.) dose of the compounds having Formula I, or pharmaceutical compositions, in accordance with methods of the present invention, will be that dose effective to result in differentiation of the affected cells, a reduction in cell proliferation, or an improvement or stabilization of the condition being treated. Approximately, 1–5 $\mu$M, more preferably about 3 $\mu$M of the compounds of the invention is sufficient to induce differentiation of cells or inhibit cell growth. Thus, dosages formulated to deliver such a concentration to cells are presently preferred. However, one of skill in the art can readily ascertain the optimum dosage to use for a particular case, using as a starting point the range delineated above.

Compounds having Formula I may be shaped together with a physiologically acceptable vehicle, carrier, excipient, binder, preservative, stabilizer, flavoring, and/or additive, into a unit dosage form. Typical examples of additives that can be used in tablets and capsules are binders such as tragacanth gum, gum arabic, corn starch and gelatin; excipients such microcrystalline cellulose, sealing agents such as corn starch, pre-gelatinized starch and alginic acid; lubricants such as magnesium stearate; sweeteners such as sucrose, lactose, and aspartase; and flavorings such as peppermint. Other additives include edible oil as a liquid carrier such as in capsules, shellac, sugar and combinations thereof such as in tablet coating).

For parenteral injection compounds of Formula I may be mixed with a vehicle to dissolve or suspend the active ingredient such as water, natural vegetable oils such as sesame oil, coconut oil, peanut oil and cottonseed oil, and synthetic oils such as ethyl oleate, and may also contain buffering agents, preservatives and antioxidants as required.

The methods of the present invention may be carried out by directly contacting cells with an effective amount of exogenously supplied compound of Formula I. Further, pro-drug precursors which are converted in vivo to a compound of Formula I are also within the scope of the invention.

The following examples are illustrative and are not meant to be limiting of the present invention.

EXAMPLES

MATERIALS

Sphingosine (from bovine brain cerebroside or bovine brain sphingomyelin), 2-amino-1-phenyl-1,3-propandiol (registry number in Chemical Abstracts: 28143-91-1), chioramphenicol base, D-threo-2-amino-1-(p-nitrophenyl)-1,3-propanediol (716-61-0), (+) phenylpropanolamine (35777-28-9), (−) phenylpropanolamine (492-41-1), (−) norpseudoepnedrine HCl (53643-20-2), (±) phenylpropanolamine HCl (154-41-6), L(−)-phenylalaninol (3182-95-4) were obtained from Sigma (St. Louis, Mich.) and D(+)-phenylalaninol was obtained from Fluka (Ronkonkoma, NY). Acyl halides of high quality were obtained from commercial sources (Aldrich or Sigma). N-acetylsphingosine (i.e. C2 ceramide) was synthesized as described previously such as in accordance with procedures described in Okazaki et al. (1990) J. Biol. Chem. 265: 15823–15831. N-acylaminoalcohols were prepared by a modified version of the Shapiro and Flowers, (1961) J. Am. Chem. Soc. 83: 3327–3332 and Arora and Radin, (1972) J. Lipid Res. 13: 86–91 procedures.

Human myelocytic leukemia HL-60 cells (20–45 passages (American Type Culture Collection, Rockville, Md., accession no. CCL 240) were obtained and grown in RPMI 1640 medium (Sigma Chemical Co., St. Louis, Mo.) containing 10% fetal calf serum at 37° C. in 5% $CO_2$ incubator at a cell density of $2 \times 10^5$ cells/mi. The cells were washed once with phosphate buffered saline (PBS) and resuspended in serum-free media containing insulin (5 mg/liter) and transferrin (5 mg/liter) for 2–3 hours before treatment with various compounds.

EXAMPLE 1

PREPARATION OF N-ACYL-AMINOALCOHOLS 1 mmole of aminoalcohol was dissolved in a mixture of 3 ml tetrahydrofuran (THF) and 5 ml of 50% sodium acetate and cooled in an ice bath; a solution of acyl chloride (1.2 mmole in 2 ml THF) was added while stirring. Stirring was continued for 30 minutes in an ice-bath and later at room temperature for 2 hr. The mixture was then maintained at 4° C. overnight. The amide was isolated by partitioning with added solvents (24 ml of chloroform, 12 ml of methanol, and 9 ml of water) and the material in the lower layer was washed with water, dried over magnesium sulfate, and the solvent was evaporated. The resulting oil or white solid was recrystallized (methanol, ethyl acetate-hexane, benzenehexane) with a 70–90% yield. All structures were verified by proton-NMR ($^1$HNMR) and mass spectroscopy (MS) spectra and purity was established by thin layer chromatography (TLC) and estimated to exceed 95%. The TLC solvent systems used were chloroform:methanol (80:20, v/v) or chloroform/methanol/acetic acid:80/4/8 (v/v). TLC spot detection was by iodine vapor or $KMnO_4$. Mass spectra/fast atom bombardment were obtained with a VG Labs, 70S Magnetic Sector Instrument; samples were prepared in α-monothioglycerol matrix and bombarded with Xenon atoms at 6 KeV. CD spectra were recorded on an ISA Inc., JOBIN YVON spectropolarimeter, from 400–200 mm (2 sec averaging time, 1 nm stop size, 2nm bandwidth, 1 cm pathlength).

$^1$HNMR spectra were obtained on a G.E. 500 MHz Omega Spectrometer. Chemical shifts (δ) are indicated in ppm relative to RMS as internal standard.

C14-L-t-APPD: MSm/z; 378(M+)

$^1$HNMR ($CDCl_3$) δ: 0.80 (3H, t, $CH_3$—C14); 1.1–1.25 (20 H, br s, $CH_2$—C14); 1.42–1.45 (2H,m, $CH_2$—C14); 2.04–2.10 (2H,m. $CH_2$—C14); 3.69–3.78 (2H,m. $CH_2$—C3); 4.02–4.06 (1H,m,HC-2); 5.0 (1H,d,HC-1); 6.16 (1H, d, NHCO); 7.30–7.26 (5H,m,Ph).

C14-L-e-APP-1: MS m/z; 362 (M+) $^1$HNMR ($CDCl_3$) δ: 0.82 (3H,t, $CH_3$—C14); 0.96 (3H,d,$CH_3$-C-3); 1.1–1.25 (20H,br s, $CH_2$—C14); 1.54–1.58 (2H,m,$CH_2$—C14); 2.12 (2H,t, $CH_2$—C14); 4.26–4.32 (1H, m, HC-2); 4.78 (1H,d, H C-1); 5.50 (1H,br s, NHCO); 7.30–7.26 (5H,m, Ph).

C14-D-e-APP-1: MS and $^1$HNMR ($CDCl_3$) spectra are identical to C14 -L-e-APP-1.

N-acetyl-C18-sphingosine (C2-Ceramide; N-acetylsphingosine):

$^1$HNMR ($CDCl_3$) δ:0.88 (3H,t,$CH_3$-C-17); 1.10–1.45 (20H,m. $CH_2$); 1.55–1.73 (2H, m, $CH_2$); 1.97–2.09 (2H,m. $CH_2$-C-6); 2.06 (3H,s,$COCH_3$); 3.71 (1H, dd, H—C-1); 3.85–4.0 (2H,m,HC-1,HC-2); 4.32 (1H,m,HC-3); 5.53 ($^1$H, dt, HC-5); 6.40 (1H, d, NHCO).

EXAMPLE 2

PREPARATION OF TRITIATED N-MYRISTOYL-PHENYLAMINOALCOHOLS (1R, 2S) 2-(N-[$^3$H]-myristoylamino)-1-phenyl-1propanol ([$^3$H] C14-L-e-APP-1) and (1S, 2R) 2-(N-[$^3$H]-myristoylamino)-1-phenyl-1-propanol ([$^3$H]C14-D-e-APP-1) were prepared following the general procedures of Example 1 for synthesis of N-acyl-amino alcohols using [$^3$H]-myristoyl chloride. Specific activity was $\sim 3 \times 10^3$ cpms/nmol. [$^3$H] myristoyl chloride was made from 9,10-[$^3$H]-myristic acid and oxalyl chloride in dry benzene.

EXAMPLE 3

EFFECT OF APPD DERIVATIVES ON HL-60 PROLIFERATION AND DIFFERENTIATION

A. EFFECTS OF THE N-ACYL CHAIN LENGTH ON CELL PROLIFERATION

HL-60 cells were treated with 3 μM of Cn-L-t-APPD with acyl chain lengths of C6, C8, C10, C12, C14, C16, and C18 (m=4, 6, 8, 10, 12, 14 and 16) in fresh ehtanol solution or with an ethanol vehicle and cell growth was determined following three days of treatment. Cell growth was quantified using a hemocytometer. Cell viability was judged by the ability to exclude trypan blue dye. Viability was always more than 80% unless otherwise described.

In comparison with a control (C2-ceramide) the N-acyl derivatives having chain lengths of C6, C8, and C18 showed little or no reduction of cell growth (105%, 104% and 116% of control values, respectively). Treatment of cells with the C10 N-acyl derivative resulted in approximately a 10% reduction of cell growth as compared to a control (90% of control cell growth). Significant reduction in cell growth was exhibited by treatment of cells with C12, C14 and C16 N-acyl derivatives resulting in approximately 40%, 15% and 65% of control cell growth, respectively. Thus, the dependence on chain length showed an optimal activity with the N-myristoyl (C14) derivative, and progressively less potency as the hydrocarbon chain either decreased or increased in length.

B. DEPENDENCE OF HL-60 GROWTH ON CONCENTRATION OF N-MYRISTOYL-L-THREO-2-AMINO-1-PHENYL-1,3-PROPANDIOL(C14-L-t-APPD)

HL-60 cells (starting cell density of $2 \times 10^5$ cells/ml) were treated with different concentrations of C14-L-t-APPD and cells were counted following 24 and 72 hours of treatment. The results are representative of three experiments. A 1 $\mu$M dose of C14-L-t-APPD had little or no effect on cell growth at 24 or 72 hours (approximately 105% and 130% of control, respectively). A 2 $\mu$M dose inhibited cell growth to approximately 65% of the control at both 24 and 72 hours. 3 and 4 $\mu$M doses of C14-L-t-APPD inhibited cell growth significantly, to less than approximately 10% of the control at both 24 and 72 hours. The $IC_{50\%}$ was approximately 2 $\mu$M (10 fmol/cell). $IC_{50\%}$ is the concentration of test compound that causes 50% inhibition of cell growth in comparison with controls. Thus, similar to results with C2-ceramide, C14-APPD inhibited cell proliferation at different durations of treatment.

C. TIME DEPENDENCE OF HL-60 GROWTH ON CHAIN LENGTH ANALOGS OF Cn-L-t-APPD

HL-60 cells (starting cell density of $2 \times 10^5$ cells/ml) were treated with 3 $\mu$M Cn-L-t-APPD derivatives with N-acyl chain lengths of C6, C8, C10, C12, C14, C16, and C18 (m=4,6,8,10, 12, 14, and 16) and cells were counted at 0, 12, 36, 60, 84 and 108 hours post treatment. The results are representative of 3 experiments.

Control cell density increased to $10 \times 10^5$/ml after 84 hours and $18 \times 10^5$/ml after 108 hours. After treatment with C2-ceramide, cell density did not increase and remained at $2 \times 10^5$/ml even at 108 hours after treatment. Treatment of cells with C6-L-t-APPD resulted in an increase of cell density to $8 \times 10^5$/ml after 60 hours, $14 \times 10^5$/ml after 84 hours and $24 \times 10^5$/ml after 108 hours. Treatment of cells with C8-L-t-APPD resulted in a similar increase in cell number ($8 \times 10^5$/ml after 60 hours, $14 \times 10^5$/ml after 84 hours and $24 \times 10^5$/ml after 108 hours). Treatment of cells with C10-L-t-APPD resulted in an increase in cell number to $8 \times 10^5$/ml after 60 hours, $12 \times 10^5$/ml after 84 hours and $20 \times 10^5$/ml after 108 hours. C12-L-t-APPD, C14-L-t-APPD and C16-L-t-APPD, however, were each able to inhibit cell growth by significant amounts. Treatment of cells with C12-L-t-APPD resulted in cell densities of $3 \times 10^5$/ml after 60 hours, $3 \times 10^5$/ml after 84 hours and $6 \times 10^5$/ml after 108 hours. Treatment of cells with C14-L-t-APPD resulted in cell densities of $1-10^5$/ml after 60 hours, $1 \times 10^5$/ml after 84 hours and $2 \times 10^5$/ml after 108 hours. Treatment of cells with C16-L-t-APPD resulted in cell densities of $4 \times 10^5$/ml after 60 hours, $7 \times 10^5$/ml after 84 hours and $12 \times 10^5$/ml after 108 hours. By contrast, treatment of cells with C18-L-t-APPD resulted in an increase of cell density to $8 \times 10^5$/ml after 60 hours, $14 \times 10^5$/ml after 84 hours and $23 \times 10^5$/ml after 108 hours.

This study shows a detailed time-course of inhibition of cell proliferation by the different N-acylated L-t-APPD derivatives. C12-L-t-APPD, C14-L-t-APPD and C16-L-t-APPD were each able to inhibit cell growth by significant amounts. However, compounds having shorter or longer acyl chain lengths had much less effect on cell growth. These results again support the chain length dependence of the activity of these compounds. The results also show that the most potent derivative (C14-L-t-APPD) is equally potent to C2-ceramide.

D. EFFECTS OF C14-L-t-APPD ON HL-60 DIFFERENTIATION

In a previous study, it was discovered that $1,25(OH)_2D_3$ caused hydrolysis of sphingomyelin in HL-60 cells with the concomitant generation of ceramide and phosphorylcholine in what appeared to be a regulated "sphingomyelin cycle". Okazaki, T., et al., *J. Biol. Chem.* 254:19076–19080 (1989). Sphingomyelin hydrolysis was suggested to play a role in HL-60 cell differentiation since the addition of exogenous bacterial sphingomyelinase potentiated the ability of subthreshold concentrations of $1,25\text{-}(OH)_2D_3$ to induce cell differentiation. Applicants subsequently discovered that ceramide functions as a lipid mediator transducing the effects of $1,25\text{-}(OH)_2D_3$ on HL-60 cell differentiation.

Since certain compounds, such as sphingosine, inhibit HL-60 cell growth but do not mimic the effects of ceramide on cell differentiation (Okazaki et al., supra), the effects of APPD derivatives on cell differentiation were determined. Therefore, 3 $\mu$M C14-L-t-APPD was applied to HL-60 cells either alone or in combination with subthreshold levels (0.3 nM) of 1,25-dihydroxyvitamin $D_3$ ($D_3$), and cell differentiation was determined at 60 and 108 hours following treatment by quantitating $H_2O_2$ generation, a marker of HL-60 differentiation. Subthreshold levels of $D_3$ refers to levels of $D_3$ that are too low to induce differentiation of HL60 cells.

$H_2O_2$ production was quantitated as described in Goodwin, B. J. and Weinberg, J. B., *J. Clin. Invest.* 70:699–706 (1982) and Pick, E. and Mizel, D. J. *Immunol. Methods* 46: 211–226 (1981). For comparison, HL60 cell differentiation obtained with 2 $\mu$M C2-ceramide alone and 0.3 nM vitamin $D_3$ are were also determined. These results are averages of two determinations and are representative of two experiments.

The results demonstrate that the treatment of HL-60 cells with 3 $\mu$M C14-L-t-APPD resulted in significant generation of $H_2O_2$ (approximately 0.3 nmol/$10^5$ cells at 60 hours and 0.5 nmol/$10^5$ cells at 108 hours). The combination of 3 $\mu$M C14-L-t-APPD and 0.3 nM 1,25-dihydroxyvitamin $D_3$ resulted in a synergistic effect on cell differentiation resulting in the generation of approximately 1.1 nmol $H_2O_2/10^5$ cells at 60 hours and 1.0 nmol $H_2O_2/10^5$ cells at 108 hours. The effects of C-14-L-t-APPD (3 $\mu$M) were nearly identical to those of 2 $\mu$M C2-ceramide which resulted in the generation of approximately 0.3 nmol $H_2O_2/10^5$ cells at both 60 and 108 hours alone, and approximately 0.9 nmol/$10^5$ cells in combination with 1,25-dihydroxyvitamin D3. Treatment of cells with 0.3 nM of 1,25-dihydroxyvitamin $D_3$ caused the generation of approximately 0.4 nmol $H_2O_2/10^5$ cells at 60 hours and 0.2 nmol/$10^5$ cells at 108 hours. A control generated less than 0.1 nmol $H_2O_2/10^5$ cells at 60 hours and no $H_2O_2$ at 108 hours

EXAMPLE 4

EFFECT OF ANPPD ON HL-60 PROLIFERATION AND DIFFERENTIATON

A. EFFECT OF N-ACYL CHAIN LENGTH ON CELL PROLIFERATION

N-acyl derivatives of 2-amino-1-(4'-nitrophenyl)-1,3-propanediol (Cn-D-t-ANPPD) were tested to determine the effects of chain length on HL-60 cell growth as described in Examples 3 A. HL-60 cells (at a starting cell density of $2 \times 10^5$ cells/ml) were treated with 3 µM of the diff analogs (C6, C8, C10, C12, C14, C16 and C18) of Cn-D-t-ANPPD, and cell growth was determined at three days. The control received no Cn-D-t-ANPPD. Treatment of HL-60 cells with C2-ceramide is included for comparison. These results are averages of two determinations and are representative of three experiments. Table II summarizes these results.

TABLE II

| SAMPLE | CELL GROWTH (% OF CONTROL) |
| --- | --- |
| Control | 100 |
| C6-D-t-ANPPD | 70 |
| C8-D-t-ANPPD | 70 |
| C10-D-t-ANPPD | 68 |
| C12-D-t-ANPPD | 4 |
| C14-D-t-ANPPD | 1 |
| C16-D-t-ANPPD | 5 |
| C18-D-t-ANPPD | 82 |
| C2-Ceramide | 20 |

Similar to the results obtained above for APPD derivatives, C14 chain analogs were found to have the greatest activity in inhibiting HL-60 cell growth (about 1% of control cell growth). The C12 and C16 chain analogs also showed significant ability to inhibit cell growth (about 4% and 5% of control growth, respectively). The data also similarly indicates progressive loss of activity with decreasing or increasing chain length. Thus, these results demonstrate the optimal chain length for the action of these phenylaminoalcohol analogs is 14. The existence of an optimal chain length is likely the product of a number of factors, such as the solubility of the different compounds, uptake by cells, partitioning into cell membranes and interaction with the heretofore unidentified molecular target for ceramide.

B. DEPENDENCE OF HL-60 CELL GROWTH ON THE CONCENTRATION OF C14-d-T-ANPPD.

HL-60 cells were treated with the indicated concentrations and cell growth was determined following three days of treatment as described in Example 3B. Table III summarizes the results of this experiment.

TABLE III

| AMOUNT (µM) | CELL GROWTH (% OF CONTROL) |
| --- | --- |
| 0 | 100 |
| 0.1 | 110 |
| 0.2 | 112 |
| 0.3 | 113 |
| 0.5 | 105 |
| 1 | 85 |
| 2 | 12 |
| 3 | 3 |
| 4 | 2 |

These results are representative of three experiments. The data indicates that 50% inhibition of cell growth occurred at a concentration of approximately 1.5 µM.

EXAMPLE 5

STRUCTURAL REQUIREMENTS

The suitability of phenylaminopropanediol derivatives as analogs of ceramide allowed further investigation of the structural requirements for ceramide-mediated biology. For these experiments, C14 (N-myristoyl) derivatives of different phenylaminoalcohols were synthesized and examined for their biologic activity. HL-60 cells (starting cell density of $2 \times 10^5$ cells/ml) were treated with 3 µM of C14 derivatives C14-L-t-APPD, C14-D-t-ANPPD, C14-D-e-APP-1, C14-L-e-APP-1, C14-APP-3 and C14-D-APP3. The structures of these compounds are provided in Table I. Cell growth was determined at 3 days as described in Example 3A. The results shown are averages of two determinations, and are representative of five different experiments. At 3 µM, these different analogs demonstrated differential activity in inhibiting HL-60 cell proliferation.

A. REQUIREMENTS FOR PRIMARY AND SECONDARY HYDROXYL GROUPS

The requirement of the hydroxyl groups was examined by using N-myristoyl derivatives of different isomers of phenylaminopropanol (APP) which contain only one hydroxyl group.

i. Requirement for Primary Hydroxyl Group

APP-1 with a secondary OH-group (corresponding to the secondary, C-3 OH group of ceramide) and APP-3 with a primary OH-group (corresponding to the primary, C-1 0H position of ceramide). The APP-1 isomers exhibited activity ranging from 15% to 87% of control cell growth. C14-D-erythro-APP-1, which exhibited 15% of control cell growth, was as effective as C2-ceramide (20% of control cell growth). The polar headgroup of this compound is similar to that of C2-ceramide except for the lack of primary hydroxyl group (at the 1 position of ceramide, the 3 position of C14-APP-1). Thus, it appears that the primary (C-1) hydroxyl group of ceramide is not essential for activity.

ii. Requirement for Secondary Hydroxyl Group

The APP-3 isomers exhibited activity of approximately 15% of control cell growth. C14-D-APP-3 and C14-L-APP-3 showed similar activity as C2-ceramide and C14-D-erythro-APP-1. These compounds lack the secondary hydroxyl of ceramide, thus suggesting that the secondary (C-3) hydroxyl group is not absolutely required for biological activity.

B. STEREOSPECIFICITY

The stereospecific requirements for the biological activity of C14 APP-1 and APP-3 analogs was also determined as described in Example 3A. C14-D-erythro-APP-1 was the most active of the APP-1 stereoisomers, exhibiting approximately 15% of control cell growth. Its enantiomer, C14-L-erythro-APP-1 showed little activity (87% of control cell growth). The racemic mixture of C14-DL-erythro-APP-1 showed intermediate activity of 60% of control cell growth. The D-threo isomer, C14-D-threo-APP-1 had intermediate activity of 49% of control cell growth. The results with these stereoisomers demonstrate the important role of the chiral center bearing the secondary hydroxyl group (i.e., carbon 1 of Formula I) in determining the activity of these molecules.

The enantiomers C14-L-APP-3 and C-14-D-APP-3 showed similar activity (15% and 14% of control cell growth respectively). This pair of enantiomers has one chiral center at the 2 position and lacks the second chiral center at the 3 position of ceramide (the 1 position of APP). The results with this pair suggest that the chirality of the carbon bearing the amino group does not modulate activity Because of the marked difference in activity between D- and L-erythro-C14-APP-1, this pair was examined further. The CD spectra of the two compounds demonstrated that they were enantiomers. Moreover, the two compounds had identical absorption spectra with identical absorption coefficients. The compounds also behaved identically on thin layer chromatography, FAB-mass spectroscopy and had identical NMR spectra.

i. Dependence of HL-60 Growth on Concentration of Enantiomers C14-D-e-APP-1 and C14-L-e-APP-1 HL-60 cells were treated as described in Example 3B. growth was determined after 3 days of treatment. The results of this experiment are summarized in Table IV.

TABLE IV

| SAMPLE | CONCENTRATION ($\mu$M) | CELL GROWTH (% OF CONTROL) |
|---|---|---|
| C14-D-e-APP-1 | 0 | 100 |
| | 1 | 100 |
| | 2 | 71 |
| | 3 | 45 |
| | 4 | 20 |
| | 5 | 10 |
| C14-L-e-APP-1 | 0 | 100 |
| | 1 | 101 |
| | 2 | 100 |
| | 3 | 99 |
| | 4 | 100 |
| | 5 | 99 |

These results are averages of two determinations, and are representative of five experiments. C14-D-erythro-APP-1 inhibited HL-60 cell growth in a dose-dependent manner with an IC50% of 2.5 $\mu$M (125 fmol/$10^5$ cells) while C14-L-erythro-APP-1 showed no activity.

ii. Effect of Enantiomers C14-D-e-APP-1 and C14-L-e-APP-1 On Differentiation of HL-60 Cells HL-60 cells were treated with 3 $\mu$M of C14-D-e-APP-1 or 3 $\mu$M C14-L-e-APP-1 for three days in accordance with the procedure described in Example 3D. Cell differentiation was determined by the ability of differentiated cells to reduce Nitro blue tetrazolium (NBT) as described in Okazaki, T. et. al., *J. Biol. Chem.* 265:15823–15831 (1990).

C14-D-erythro-APP-1 was a potent inducer of HL-60 differentiation with 42% of the cells acquiring the ability to reduce NBT compared to 10% of control cells. This level of differentiation was similar to that achieved by C2-ceramide. On the other hand, C14-L-erythro-APP-1 showed little activity over control (12% as compared to 10% of control cells). These results are averages of two determinations and are representative of two different experiments.

In studies using [$^3$H]-labeled C14-D-e-APP-1 and C14-L-e-APP-1, uptake of the two compounds was nearly identical with 21% of [$_3$H]-C14-D-e-APP-1 taken up and 20% of [$_3$H]-C14-L-e-APP-1 taken up. Thus, enantiomers were comparable and therefore the differential effects of the two compounds appear to be a result of differential interactions with cellular targets.

What is claimed is:

1. A method of inducing mammalian cell differentiation, comprising contacting a mammalian cell capable of undergoing differentiation with an amount of a compound effective to induce differentiation, said compound having the formula:

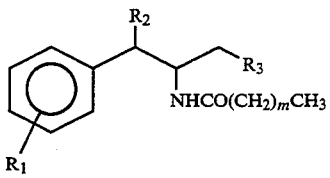

wherein
$R_1$ is H, $NO_2$, OH, chlorine, bromine or fluorine;
$R_2$ is H, OH or methoxy;
$R_3$ is H or OH; and
m is an integer from about 10 to about 14.

2. The method of claim 1 wherein $R_1$ is H of $NO_2$, $R_2$ is H or OH, $R_3$ is H or OH and m is an integer from about 10 to about 14.

3. The method of claim 2 wherein m is 12.

4. The method of claim 1 wherein $R_1$ is H, $R_2$ is OH, $R_3$ is OH and m is 12.

5. The method of claim 1 wherein $R_1$ is $NO_2$, $R_2$ is OH, $R_3$ is OH and m is 12.

6. The method of claim 1 wherein $R_1$ is H, $R_2$ is H, $R_3$ is OH and m is 12.

7. The method of claim 1 wherein $R_1$ is H, $R_2$ is OH, $R_3$ is H and m is 12.

8. The method of claim 1 wherein said cell is a leukemic lymphocyte.

9. The method of claim 1 wherein said cell is a hyperproliferative basal cell residing in the skin of a mammal and said contacting is carried out upon the skin of the mammal.

10. A method of altering the phenotype of a mammalian cell, comprising contacting a mammalian cell having a transformed phenotype with an amount of a compound effective to alter the phenotype of the cell to a non-transformed phenotype, said compound having the formula:

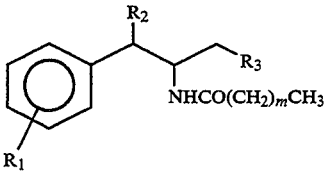

wherein
$R_1$ is H, $NO_2$, OH, chlorine, bromine or fluorine;
$R_2$ is H, OH or methoxy;
$R_3$ is H or OH; and
m is an integer from about 10 to about 14.

11. The method of claim 10 wherein $R_1$ is H of $NO_2$, $R_2$ is H or OH, $R_3$ is H or OH and m is an integer from about 10 to about 14.

12. The method of claim 11 wherein m is 12.

13. The method of claim 10 wherein $R_1$ is H, $R_2$ is OH, $R_3$ is OH and m is 12.

14. The method of claim 10 wherein $R_1$ is $NO_2$, $R_2$ is OH, $R_3$ is OH and m is 12.

15. The method of claim 10 wherein $R_1$ is H, $R_2$ is H, $R_3$ is OH and m is 12.

16. The method of claim 10 wherein $R_1$ is H, $R_2$ is OH, $R_3$ is H and m is 12.

17. The method of claim 10 wherein said cell is a leukemic lymphocyte.

* * * * *